United States Patent
Hopper et al.

(10) Patent No.: US 6,459,929 B1
(45) Date of Patent: Oct. 1, 2002

(54) IMPLANTABLE CARDIAC RHYTHM MANAGEMENT DEVICE FOR ASSESSING STATUS OF CHF PATIENTS

(75) Inventors: Donald L. Hopper, Maple Grove; Jeffrey E. Stahmann, Ramsey; Bruce R. Jones, Hopkins; James P. Nelson, Lino Lakes, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/547,519

(22) Filed: Apr. 12, 2000

Related U.S. Application Data

(63) Continuation-in-part of application No. 09/434,009, filed on Nov. 4, 1999, now Pat. No. 6,275,727.

(51) Int. Cl.[7] .............................................. A61B 5/0205
(52) U.S. Cl. ..................... 600/513; 600/510; 607/18; 607/20
(58) Field of Search ................. 607/17–20; 600/547, 600/508, 513, 483, 481

(56) References Cited

U.S. PATENT DOCUMENTS 5,063,927 A * 11/1991 Webb et al. ................... 607/18

* cited by examiner

*Primary Examiner*—George R. Evanisko
(74) *Attorney, Agent, or Firm*—Nikolai & Mersereau, P.A.; Thomas J. Nikolai

(57) ABSTRACT

A method and apparatus for providing congestive heart failure therapy status. An electronic device, preferably a cardiac rhythm management device, capable of measuring transthoracic impedance and for sensing a level of physical activity is implanted in a patient. The transthoracic impedance signal is processed to obtain an estimate of the subject's minute ventilation, respiratory rate, tidal volume, inspiratory rate and expiratory rate. From accelerometer measured activity, an estimate is obtained of oxygen uptake, carbon dioxide production and work rate. Ratios of tidal volume to respiratory rate, tidal volume to inspiratory time, tidal volume to expiratory time, heart rate to minute ventilation, respiratory rate to minute ventilation, tidal volume to minute ventilation, minute ventilation to oxygen uptake, minute ventilation to carbon dioxide production, minute ventilation to work rate, heart rate to work rate, oxygen uptake to heart rate and other ratios are meaningful status indicators for assessing the efficacy of particular therapy regimens to CHF patients.

6 Claims, 1 Drawing Sheet

IMPLANTABLE CARDIAC RHYTHM MANAGEMENT DEVICE FOR ASSESSING STATUS OF CHF PATIENTS This patent application is a continuation-in-part of copending application Ser. No. 09/434,009 filed Nov. 4, 1999, now U.S. Pat. No. 6,275,727.

BACKGROUND OF THE INVENTION

1. Field of the Invention

This invention relates generally to an apparatus and method for treating and assessing the efficacy of such treatment of CHF patients, and more particularly to an improved cardiac rhythm management device incorporating circuitry for sensing respiratory, heart rate and/or activity-related parameters.

2. Discussion of the Related Art

"Cardiac Pacemakers" and "Cardiac Rhythm Management" (CRM) devices are both used as generic terms for pacemakers and defibrillators. CRMs have long been used in the treatment of bradycardia and tachycardia, but only more recently CRMs have been specifically designed to enhance the hemodynamic performance of the heart for patients suffering from CHF. Pacemakers designed for treatment of bradycardia have incorporated a variety of physiologic sensors whereby the pacing rate of the pacemaker can be made to vary automatically with changes in physiologic demand. Thus, for example, the Hauck et al. U.S. Pat. No. 5,318,597 describes a rate adaptive pacemaker in which the pacing rate is adjusted in accordance with changes in a patient's minute ventilation. Means are provided in the CRM for measuring variations in transthoracic impedance and for processing of the impedance signal to extract a minute ventilation signal that is used to vary the pacing rate of an implantable pacemaker between lower and upper programmed rate limit values in that there is a direct correlation between a patient's minute ventilation and the body's hemodynamic demand.

Other rate adaptive CRMs have incorporated some form of an activity sensor, such as an accelerometer, for developing a control signal that varies with a patient's level of physical activity. This control signal is then used to vary the pacing rate of a rate adaptive CRM device to maintain an appropriate pacing rate for the level of exercise being exerted.

In implantable CRM devices especially designed for treating patients with CHF, one approach that has proved successful involves the automatic optimization of the AV delay of an implantable, dual-chamber pacemaker. For a general description of the prior art relating to pacemakers for treating CHF, reference is made to the Baumann U.S. Pat. No. 5,800,471, the teachings of which are incorporated herein by reference as if set forth in full.

The present invention constitutes a departure from the related art in that even though the apparatus employed incorporates circuitry for implementing impedance plethysmography in generating a signal component relating to minute ventilation and an accelerometer responsive to patient activity, the information derived from these sensors is used to monitor a CHF patient's status so that the efficacy of a change in pacing therapy or drug therapy can be read from the implanted device periodically for review and analysis by a medical professional.

Studies have shown that patients with chronic heart failure are limited by exertional dyspnea and exercise intolerance. Such patients often exhibit elevated ventilatory response to exercise, which can be characterized by a steeper slope relating minute ventilation to carbon dioxide output during exercise. In addition to the increased ventilation, such patients have also been noted to have an abnormal breathing pattern, such that at a given minute ventilation, respiratory rate is increased while the change in tidal volume is less significant compared with normal subjects. The ventilatory response to exercise, as characterized by the regression slope relating minute ventilation to carbon dioxide output during exercise by CHF patients, has been found to be significantly higher in such patients than for normal subjects. See "The Role of Peripheral Chemoreflex in Chronic Congestive Heart Failure" by T. P. Chua et al, CHF; November/December 1997; pp. 22–28.

The method of the present invention is carried out by implanting in the patient a CRM device of a type incorporating a transthoracic impedance sensor, a patient activity sensor and a processor operatively coupled to the transthoracic impedance sensor for controlling the delivery of cardiac stimulating pulses to the patient's heart. The processor is programmed to permit it to derive a plurality of respiratory parameters from signals produced by the transthoracic impedance sensor. A telemetry link may also be provided to allow the respiratory parameters or signals relating thereto to be transmitted to an external monitor for viewing by a medical professional. Either the processor forming a part of the implanted CRM device or a processor contained within the external monitor computes predetermined ratio values involving the derived respiratory parameters as congestive heart failure therapy status indicators.

The apparatus involved may further include an activity sensor connected to the microprocessor for deriving a plurality of physiologic parameters based upon the signal output of the activity sensor. The activity sensor derived parameters may also be telemetered to the external monitor for display or for further processing and display.

Meaningful ratios that serve as CHF status indicators include: ventilatory tidal volume to respiratory rate ($V_t/RR$); ventilatory tidal volume to inspiratory time ($V_t/T_i$); ventilatory tidal volume to expiratory time ($V_t/T_e$); minute ventilation to carbon dioxide output ($MV/VCO_2$); respiratory rate to minute ventilation ($RR/MV$); and tidal volume to minute ventilation ($V_t/MV$). Another ratio of interest is $O_2$ pulse, which is the amount of oxygen uptake per heartbeat ($VO_2/HR$).

Other researchers have found a high correlation between oxygen consumption ($VO_2$) and carbon dioxide production ($VCO_2$) with heart rate and physical activity to the point where it is possible to estimate these respiratory parameters based on measured heart rate and physical activity. See, for example, "Combined Heart Rate and Activity Improve Estimates of Oxygen Consumption in Carbon Dioxide Production Rate" by Jon K. Moon and Nancy F. Butte, *J. Applied Physiology*, 81(4:1754–1761) 1996. The present invention takes advantage of such high correlation, providing a way in which a particular pacing or drug therapy affects the status of CHF patients in whom the present invention is utilized.

SUMMARY OF THE INVENTION

The present invention provides a method and apparatus for monitoring a patient's status of congestive heart failure. The method is carried out by first implanting in the patient an electronic device capable of measuring transthoracic impedance and for sensing a level of physical activity. The transthoracic impedance signal is then processed such that an estimate is derived of the patient's minute ventilation, respiratory rate and tidal volume. Likewise, the oxygen uptake ($VO_2$) and carbon dioxide production values ($VCO_2$) are estimated from the accelerometer measured activity. It has been found that by calculating a ratio of tidal volume to respiratory rate, a first CHF status indicator is obtained.

Also, once tidal volume information from a patient is arrived at, his or her inspiratory time can also be derived. The ratio of tidal volume to inspiratory time is found to comprise a second congestive heart failure status indicator that is meaningful. The ratio of minute ventilation to carbon dioxide production can be derived as a third congestive heart failure status indicator. Similarly, the ratio of oxygen uptake to heart rate is found to be a further CHF status indicator.

The invention also contemplates the use of the CHF status indicators (ratios) in the closed-loop control of a CRM device that for example may adjust a pacing parameter to optimize the benefit afforded by the pacing therapy.

The foregoing features, objects and advantages of the invention will become apparent to those skilled in the art from the following detailed description of a preferred embodiment, especially when considered in conjunction with the accompanying description and drawings.

DETAILED DESCRIPTION OF THE INVENTION

Figure 1:
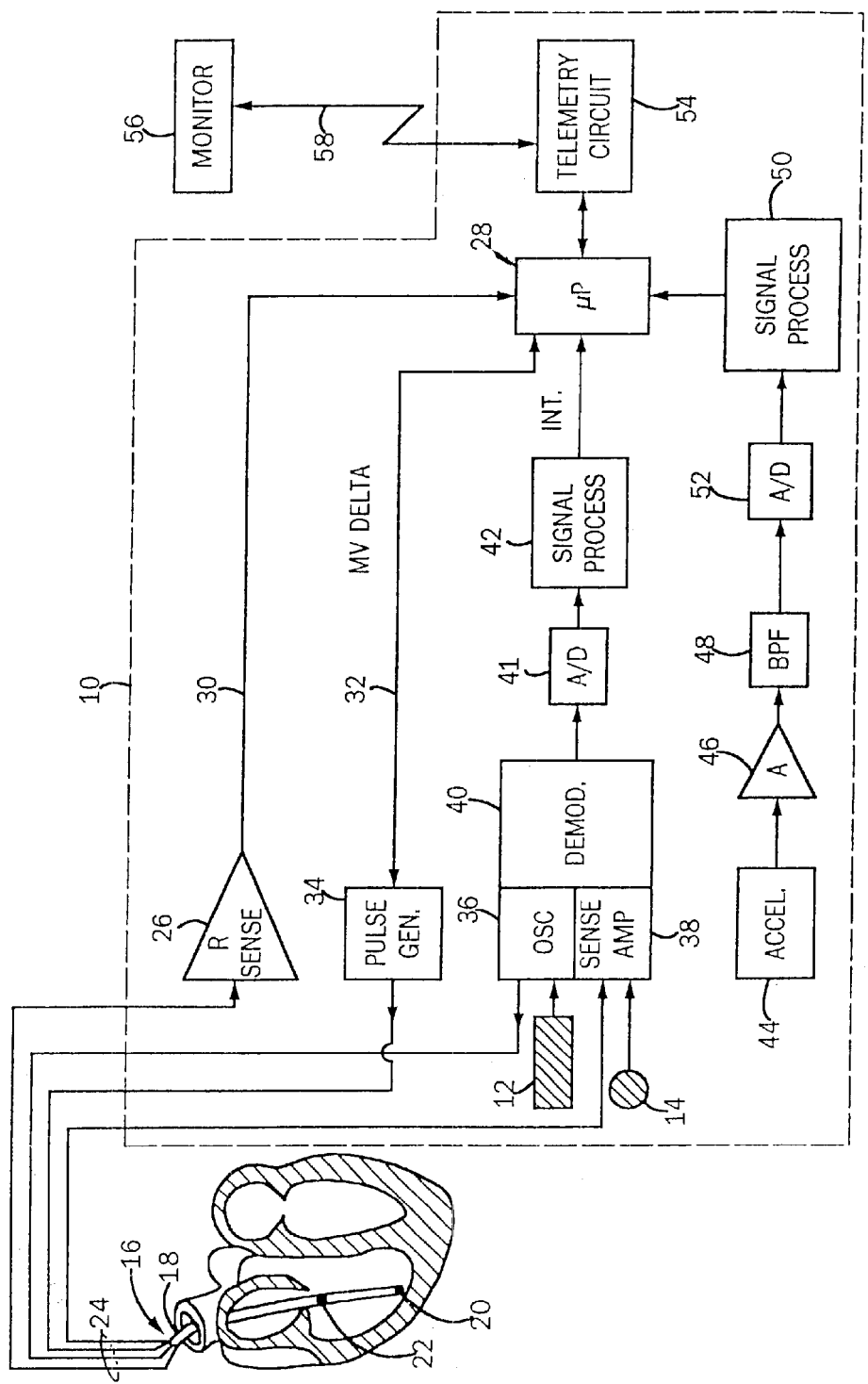
FIG. 1, is a block diagram representation of a CRM device configured in accordance with the present invention.

The present invention is applicable to a monitoring a variety of conditions of the heart. The invention is generally described in the context of an implantable cardiac rhythm management device configured to monitor chronic heart failure (CHF) patients for illustrative purposes only. The appended claims are not intended to be limited to any specific example or embodiment described in this patent.

Referring to FIG. 1 there is illustrated by means of an electrical schematic block diagram the hardware platform to carry out the method of the present invention can be. Shown enclosed by a broken line box 10 is a CRM device having electrodes 12 and 14 disposed thereon. Electrode 12 may comprise an uninsulated portion of the metal, typically titanium, hermetically sealed housing while electrode 14 may be disposed on the device's header. CRM device 10 is adapted to be coupled to a patient's heart via an electrical lead assembly 16 comprising an body member 18 having a distal tip electrode 20 and a ring electrode 22 affixed to the surface thereof. Body member 18 is typically a flexible elongated and tubular and composed of a biocompatible material. Extending the length of the lead are electrical conductors 24 that connect through electrical contacts in the lead barrel to the internal circuitry of the CRM device.

Contained within the hermetically sealed housing is a R-wave sensing amplifier 26 that picks up and amplifies ventricular depolarization signals picked up by the electrode 20. The output from the sense amplifier is applied as an input to a microprocessor circuit 28 by way of conductor 30. The microprocessor, following a stored program, provides a control signal on line 32 to a pulse generator 34 whose output signal is applied over one of the conductors 24 to the tip electrode 20 for stimulating and thereby evoking a paced response from the heart.

In accordance with the present invention, circuitry is also provided for measuring impedance changes within at least one chamber of the heart due to the influx and outflow of blood. In this regard, there is provided an oscillator 36 which, when activated, produces an alternating current of a predetermined frequency, typically in a range of from about 2000 Hz to 5000 Hz and of an amplitude below about 10 microamperes, which insures that the output from the oscillator will not stimulate heart tissue. This signal is preferably applied between the indifferent electrode 12 on the implanted CRM device and the ring electrode 22 on the lead and comprises an AC carrier signal that is modulated by the influx and outflow blood from the right ventricle. The modulated carrier signal is developed between the tip electrode 20 and the indifferent electrode 14 on the device's header and is amplified by sense amplifier 38 and then demodulated by demodulator circuit 40 to remove the modulating envelope from the carrier. The envelope signal is a measure of instantaneous impedance as a function of time.

The impedance vs. time (Z vs. t) analog signal is converted to a digital format by A/D converter 41 and is then applied to a signal processing circuit 42 which comprises a peak/valley/zero cross detector. When a zero cross is detected, the circuit 42 calculates the preceding peak-to-valley amplitude and issues an interrupt signal to the microprocessor 28. Upon receiving this interrupt, the microprocessor fetches the peak-to-valley amplitude from the signal processing circuit 42 and sums the absolute values of the peak-to-valley amplitudes over an eight-second interval. This eight-second sum of the peak-to-valley amplitudes comprises the sensor input that is used in establishing the minute ventilation delta signal fed over line 32 to the pulse generator 34 for adjusting the rate at which the pulse generator issues cardiac stimulating pulses to the heart.

The aforereferenced Hauck et al. '597 patent, hereby incorporated by reference, describes a system for developing a delta rate signal for a rate adaptive pacemaker based upon variations in minute ventilation index. This patent describes, in detail, how a transthoracic impedance waveform can be signal processed to derive respiratory related factors including respiratory rate (RR), tidal volume ($V_t$) inspiratory time ($T_i$), expiratory time ($T_e$) and minute ventilation (MV) and need not be repeated here. It is also known from the prior art that estimates of $VO_2$ and $VCO_2$ can be derived from patient activity information provided by a patient worn accelerometer. Reference is again made to the Moon et al. publication, supra.

The CRM device 10 also includes an activity sensor in the form of an integrated silicon accelerometer 44 that is bonded to a ceramic circuit board contained within the housing of the CRM device. The accelerometer includes a mass suspended by four leaf spring elements from a frame. The springs each include a piezoresistive element forming the four legs of a Wheatstone bridge which becomes unbalanced from displacement of the mass due to acceleration forces in a direction perpendicular to the frame.

To conserve battery power, the Wheatstone bridge is energized in a pulse mode where a predetermined voltage is applied across it for only a short period of time, typically 15 microseconds, and at a repetition rate of about 146 Hz. The raw accelerometer output from device 44 is then amplified by amplifier 46 before being applied to a switched capacitor bandpass filter 48. The pass band of the filter 48 effectively excludes motion artifacts due to external noise sources while allowing passage of signal components whose frequencies are related to body motion due to exercise.

The output from the bandpass filter 48 is converted to a digital quantity by A/D converter 52 and then signal processed by circuits before being applied to the microprocessor 28.

The CRM device 10 further includes a telemetry circuit 54 of known construction which allows information stored in the microprocessor's RAM memory banks to be read out transcutaneously to an external monitor 56 for viewing by a medical professional. Moreover, the telemetry link 58 allows programmable operands of the pacemaker to be altered following implantation of the CRM device.

In accordance with the present invention, we provide a CRM device which, when implanted in a patient, provides for the read-out of both respiratory data and activity data, whereby a physician or other caregiver can compute, as ratios, a number of features indicative of CHF patient status. Included are respiratory rate to minute ventilation (RR/MV); tidal volume to minute ventilation ($T_i$/MV); heart rate to minute ventilation (HR/MV), heart rate to work rate (HR/WR), minute ventilation to oxygen uptake (MV/VO$_2$) and minute ventilation to work rate (MV/WR). Other computed ratios, such as tidal volume to inspiratory time ($V_t/T_i$), tidal volume to expiratory time ($V_t/T_e$), minute ventilation to CO$_2$ production (MV/CO$_2$) and tidal volume to respiratory rate ($V_t$/RR) also prove meaningful and the factors are readily obtained from a state-of-the-art rate-adaptive pacemaker incorporating an accelerometer and impedance measuring circuits. In addition, the ratio of oxygen uptake to heart rate (VO$_2$/HR) could also be used wherein oxygen uptake could be measured with an accelerometer and heart rate being measured by the CRM device. Further, a factor indicative of the patient's body mass index (BMI) could also be incorporated into the measurements to increase the specificity of the calculations.

If an increase in the HR/MV ratio is detected following a change in therapy, it is indicative of worsening of CHF and suggests that the therapy was ineffective. Likewise, should the $V_t$/RR ratio decrease, it suggests that the patient's condition has worsened and that the therapy should be modified accordingly.

The $V_t/T_i$ ratio is a good indicator of change in CHF status. An increase in this ratio following a change in pacing therapy or drug therapy is indicative that the change was counter-productive.

The MV/VCO$_2$ ratio or slope increases as a patient's CHF condition worsens. The slope for normal persons is about 0.025 while a typical CHF patient will exhibit a slope of 0.035 or higher at rest and at relatively low levels of exercise.

The RR/MV ratio gives the percentage of current MV due to increases or decreases in respiratory rate. An increase in this ratio would be indicative of a CHF patient's worsening condition.

The $V_t$/MV ratio gives the percentage of current MV due to increases or decreases in tidal volume. A decrease in this ratio would be indicative of a CHF patient's worsening condition.

The above listed ratios are listed for exemplary purposes. Those skilled in the art will recognize that other ratios derived from the above listed variables and derivatives of those variables will also be indicative of a CHF patient's condition.

It can be seen that by data logging accelerometer data (activity) and transthoracic impedance within an implanted CRM device for subsequent readout and processing, valuable information on CHF patient condition can be stored over a prolonged period of time and then telemetered to a healthcare professional via the implanted device's telemetry link.

Alternatively, one or more of the derived ratios can be compared to corresponding ratio(s) previously computed and stored to determined whether a change in therapy has proven beneficial or has resulted in a worsening of the patient's CHF status. If so, a programmable parameter of the CRM can be adjusted accordingly in either a closed-loop (automatic) or open-loop (manual) fashion.

This invention has been described in considerable detail to provide those skilled in the art with the information needed to make and use the invention. However, it is to be understood that the invention can be carried out by specifically different ratios, equipment and devices, and that various modifications, both as to the ratios, equipment and operating procedures, can be accomplished without departing from the scope of the invention itself.

What is claimed is:

1. Apparatus for monitoring a patient's status of congestive heart failure comprising:

(a) an implantable cardiac rhythm management device having a transthoracic impedance sensor for producing signals related to the pumping action of the heart and respiratory activity, a patient activity sensor for producing signals related to patient activity levels and a microprocessor, connected to the transthoracic impedance sensor and the patient's activity sensor, for controlling the delivery of cardiac stimulating pulses to the patient's heart;

(b) means including the microprocessor for deriving a plurality of respiratory parameters from signals produced by the transthoracic impedance sensor;

(c) an external monitor; and (d) means for telemetrically transmitting digital information relating to the respiratory parameters from the implantable cardiac rhythm management device to the external monitor, said external monitor including means for computing and displaying predetermined ratios of the respiratory parameters as congestive heart failure status indicators.

2. The apparatus of claim 1 and further including:

(a) means including the microprocessor for deriving a plurality of physiologic parameters from the signals produced by and the activity sensor; and wherein the means for telemetrically transmitting digital information relating to respiratory activity further selectively telemetrically transmits digital information relating to said physiologic parameters to the external monitor wherein the means for computing and displaying predetermined ratios computes and displays ratios of the physiologic parameters as congestive heart failure status indicators.

3. The apparatus of claim 2 wherein the plurality of physiologic parameters include heart rate, oxygen uptake, and carbon dioxide output.

4. The apparatus of claim 3 wherein the ratios and wherein the cardiac device determines heart rate of the physiologic parameters include minute ventilation to carbon dioxide output and oxygen uptake to heart rate.

5. The apparatus of claim 1 wherein the respiratory parameters include minute ventilation, respiratory rate, tidal volume and inspiratory time.

6. The apparatus of claim 5 wherein the predetermined ratio values of respiratory parameters include the ratio of tidal volume to respiratory rate and tidal volume to inspiratory time, tidal volume to minute ventilation and respiratory rate to minute ventilation.

* * * * *

UNITED STATES PATENT AND TRADEMARK OFFICE
CERTIFICATE OF CORRECTION

PATENT NO.    : 6,459,929 B1
DATED         : October 1, 2002
INVENTOR(S)   : Donald L. Hopper et al.

It is certified that error appears in the above-identified patent and that said Letters Patent is hereby corrected as shown below:

<u>Column 6,</u>
Lines 51-54, claims 3 and 4 should read as follows:
3. The apparatus of claim 2 wherein the plurality of physiologic parameters include oxygen uptake and carbon dioxide output, and wherein the cardiac device determines heart rate.

4. The apparatus of claim 3 wherein the ratios of the physiologic parameters include minute ventilation to carbon dioxide output and oxygen uptake to heart rate.

Signed and Sealed this

Seventeenth Day of December, 2002

JAMES E. ROGAN
*Director of the United States Patent and Trademark Office*